US006602420B2

(12) United States Patent
Kearney et al.

(10) Patent No.: US 6,602,420 B2
(45) Date of Patent: *Aug. 5, 2003

(54) METHOD OF DISPLACEMENT CHROMATOGRAPHY

(75) Inventors: Michael M. Kearney, Twin Falls, ID (US); Vadim N. Kochergin, Twin Falls, ID (US)

(73) Assignee: Amalgamated Research, Inc., Twin Falls, ID (US)

( * ) Notice: Subject to any disclaimer, the term of this patent is extended or adjusted under 35 U.S.C. 154(b) by 135 days.

This patent is subject to a terminal disclaimer.

(21) Appl. No.: 09/956,580

(22) Filed: Sep. 19, 2001

(65) Prior Publication Data

US 2002/0027104 A1 Mar. 7, 2002

Related U.S. Application Data

(62) Division of application No. 09/355,415, filed as application No. PCT/US98/01512 on Jan. 28, 1998, now Pat. No. 6,379,554.
(60) Provisional application No. 60/036,603, filed on Jan. 29, 1997.

(51) Int. Cl.[7] .............................................. B01D 15/08
(52) U.S. Cl. .................... 210/659; 210/198.2; 127/46.2; 127/463
(58) Field of Search ................................ 210/635, 656, 210/659, 198.2; 127/46.2, 46.3

(56) References Cited

U.S. PATENT DOCUMENTS

| 2,985,589 A | 5/1961 | Broughton et al. ............ 210/34 |
| 4,001,112 A | 1/1977 | Barker et al. .............. 210/31 C |
| 4,104,078 A | 8/1978 | Barker et al. ................ 210/656 |
| 4,213,913 A | 7/1980 | de Rosset ................. 560/428.5 |
| 4,313,015 A | 1/1982 | Broughton ................... 585/828 |
| 4,332,623 A | 6/1982 | Ando et al. ................. 127/46.2 |
| 4,359,430 A | 11/1982 | Heikkila et al. ........ 260/501.13 |
| 4,379,751 A | 4/1983 | Yoritomi et al. ............. 210/659 |
| 4,405,455 A | 9/1983 | Ando et al. .................. 210/191 |
| 4,412,866 A | 11/1983 | Schoenrock et al. ........ 127/46.2 |
| 4,519,845 A | 5/1985 | Ou ............................. 127/46.2 |
| 4,631,129 A | 12/1986 | Heikkila ...................... 210/635 |

(List continued on next page.)

FOREIGN PATENT DOCUMENTS

| EP | 0411780 A2 | 2/1991 | .................. 210/659 |
| JP | 02124895 | 5/1990 | .................. 210/652 |
| WO | WO94/17213 | 8/1994 | .................. 210/659 |
| WO | WO96/10650 | 4/1996 | .................. 210/659 |

OTHER PUBLICATIONS

Wankat, Large–Scale Adsorption and Chromatopgraphy, 1986, pp. 112–113, CRC Press, Inc., United States.
Stark, Ion Exclusion Purification of Molasses, Journal of the A.S.S.B.T., 1965, pp. 492–502, vol. 13, No. 6.
Schoenrock, The Development and Application of Continuous Ion Exclusion, 1987, pp. 1–12.
Hongisto, Some Technical and Economic Aspects of the Chromatographic Separation of Sugar Solutions, British Sugar Corporation Limited 23rd Technical Conference, 1976, pp. D1–D24.
New Technology, IWT ADSEP System, Advanced Technology in Liquid Processing, vol. 1, No. 1, Mar. 4, 1983.
Sayama et al, Production of Raffinose: A New By—Product of the Beet Sugar Industry, 1992.

Primary Examiner—Ernest G. Therkorn
(74) Attorney, Agent, or Firm—TraskBritt (57) ABSTRACT

A plurality of chromatographic separation operations, including a first simulated moving bed operation, are coupled into a process which functions, preferably through the application of continuous displacement chromatography, to recover a fraction rich in small organic molecules, notably betaine and/or invert from sucrose solutions, enabling the subsequent production of a high purity sucrose product.

10 Claims, 4 Drawing Sheets

U.S. PATENT DOCUMENTS

| | | |
|---|---|---|
| 4,940,548 A | 7/1990 | Zinnen ........................ 210/656 |
| 5,102,553 A | 4/1992 | Kearney et al. ............. 210/659 |
| 5,127,957 A | 7/1992 | Heikkila et al. ............... 127/47 |
| 5,177,008 A | 1/1993 | Kampen ..................... 435/139 |
| 5,382,294 A | 1/1995 | Rimedio et al. ............... 127/42 |
| 5,384,035 A | 1/1995 | Smolnik et al. ............. 210/635 |
| 5,730,877 A | 3/1998 | Heikkila et al. ............. 210/659 |
| 5,795,398 A | 8/1998 | Hyoky et al. ............... 127/46.1 |
| 5,851,405 A | 12/1998 | Paananen et al. ........... 210/724 |
| 6,093,326 A | 7/2000 | Heikkila et al. ............. 210/659 |

METHOD OF DISPLACEMENT CHROMATOGRAPHY

CROSS-REFERENCE TO RELATED APPLICATIONS

This application is a divisional of application Ser. No. 09/355,415, filed Nov. 18, 1999, now U.S. Pat. No. 6,379,554, which is a U.S. national entry application of PCT application No. PCT/US98/01512, filed on Jan. 28, 1998 which claims the benefit of the filing date of U.S. provisional patent application Ser. No. 60/036,603, filed Jan. 29, 1997, for "COUPLED LOOP CHROMATOGRAPHY FOR MULTI COMPONENT SEPARATION" under the provisions of 35 U.S.C. 119(e).

BACKGROUND OF THE INVENTION

1. Technical Field

This invention pertains to a process of simulated moving bed (SMB) chromatography. It is particularly directed to operation of a simulated moving bed in coupled relation to a second chromatographic separation process. It provides for the recovery of a betaine and/or invert fraction from sugar solutions and the coupled production of a high purity sucrose product.

2. Background Art

U.S. Pat. No. 4,412,866 describes the operation of an SMB to separate the components of a feed stock. A resin bed is divided into a series of discrete vessels, each of which functions as a zone within a circulation loop. A manifold system connects the vessels and directs in appropriate sequence to (or from) each vessel each of the four media accommodated by the process. Those media are generally referred to as feed stock, eluent, extract and raffinate, respectively. As applied to a sugar factory, a typical feed stock is sucrose solution, the eluent is water, the extract is an aqueous solution of sucrose and the raffinate is an aqueous solution containing nonsucrose, such as salts and high molecular weight compounds. The SMB disclosed by the '866 patent is of the type sometimes referred to as a "continuous SMB" to distinguish it from another type, sometimes referred to as a"sequential SMB." Unless otherwise indicated, the term "SMB" is used in this disclosure to denote a continuous SMB.

The largest single loss of sugar values from a typical sugar factory is attributable to molasses formation. Molasses comprises the byproduct (or waste) stream remaining after repeated crystallization procedures are applied to recover purified sugar. This molasses is typically of such low purity that further crystallization procedures for the recovery of additional sugar are economically impractical. SMB arrangements similar to those disclosed by the '866 patent are used in sugar factories to process molasses, typically producing a product fraction of relatively high (e.g., 90%) purity and low ash content and a byproduct fraction, comprising, typically, 40–50% of the feed, of relatively low purity and low ash content. (As used in the sugar industry, "purity" specifies percent by weight sucrose of the solids contained in a sample, on a dry weight basis.)

In the sugar beet industry, the byproduct fraction contains most of the betaine values of the molasses feed. Betaine, being the most abundant nitrogenous compound found in molasses, has been recognized as a commercially useful byproduct, notably for use in animal feeds. In the sugar cane industry, the byproduct fraction contains most of the invert sugar (i.e., glucose and fructose) values of the molasses feed. The invert is a valuable digestible carbohydrate. As used herein, the term "invert" refers to "invert sugar" (a mixture of glucose and fructose formed in equal quantities by the hydrolysis of sucrose).

In the typical operation of SMB chromatography, the product sucrose fraction (extract) is contaminated to some extent by betaine and/or invert. Such contamination reduces the recovery of these valuable byproducts and reduces the purity of the sucrose product. This disadvantage is attributable to the steps inherent in typical SMB operation. The SMB is initially inventoried with solids to an equilibrium state, and, thereafter, feed and eluent are fed into the continuously recycling inventory while extract and raffinate are withdrawn from the recycling inventory. In the context of this disclosure, the term "inventory" refers to the distribution and identity of chemical species constituting the recycle stream. This recycling of inventory is generally a very favorable aspect of the SMB, because material is subjected to a very long chromatographic path for separation, dependent upon chosen recycle rates and inventory levels. As a result, difficult-to-remove materials, such as certain color compounds, are efficiently removed. In comparison, inventory build-up and long separation path length (due to circulation) are inconsistent with batch chromatography. Eluent use is also much lower in SMB chromatography because the eluent is continuously recycled (eluent phase) as part of the internal inventory.

Unfortunately, providing a continuous, quickly recycling, internal configuration results in only two well-separated components, one on each end of the separation profile. Some nonsucroses, such as ash and high molecular weight compounds, move much more quickly than sucrose through the monovalent form ion exchange separation resins typically employed and, therefore, move to the front of the recirculating separation profile. Some other nonsucroses, such as betaine, invert and certain amino acids, move much more slowly than sucrose through these resins. As a consequence, either the faster moving nonsucroses or the slower moving nonsucroses must always be crossing through the separated sucrose, thereby contaminating the sucrose.

The extract obtained from the chromatography of sucrose solutions is conventionally subjected to crystallization procedures, resulting in an acceptably pure saleable sugar product. The highest present day commercial standards for overall recovery of crystallized sucrose from beet molasses suggest a chromatography efficiency of 92 purity sucrose at 90% recovery. At this purity level, subsequent recovery by crystallization procedures is typically about 87%, with a loss of some sucrose to a second molasses (60 purity). Overall, a "superior" combined result of conventional chromatography and crystallization procedures has been the recovery of up to about 78% of the sucrose content of the initial molasses as crystalized sucrose.

U.S. Pat. Nos. 4,359,430 and 5,127,957 describe methods for the recovery of a betaine fraction from various sources, such as the molasses produced by a sugar factory. The '957 patent discloses a discontinuous circulation, batch-wise operation. The method involves shutting off all input and output streams to the SMB while maintaining circulation through the resin bed. Thereafter, circulation is halted, and water and/or molasses feed are introduced at specified locations to displace betaine, sucrose and rest molasses from separate columns in the loop. The "circulation" taught by the '957 patent is not a true recycle conventional to continuous SMB systems; it merely functions to displace the separation profile to an assigned location in the resin bed. By contrast, the continuous recycle stream, which is essential to a continuous SMB operation, circulates the separation profile continuously through the resin bed.

International Application WO 96/10650 describes a proposed betaine-recovery process which accepts the conventional 92 purity standard as the applicable goal for the sucrose fraction of the process. The WO 96/10650 process contains no suggestion that a sucrose fraction free from significant quantities of betaine or other small organic molecules be collected.

Ordinarily, the chromatography of sucrose-containing mixtures, such as sugar beet molasses, involves variations of elution chromatography. The feed mixture enters a chromatographic configuration of some type, and due to a preferential adsorption, the sucrose product is collected somewhere roughly from the middle to the trailing edge of the developed elution profile. As an elution system is loaded higher and higher with feed mixture, or as eluent is progressively reduced, the bands of separated material broaden and increasingly overlap. As a consequence, separation deteriorates. Inevitably, the efficiency of elution chromatography is limited by mixture loading and elution volume.

It is understood by those skilled in batch chromatography (as opposed to simulated moving bed chromatography) that very high column loading under appropriate conditions provides potentially advantageous specific effects. At large sample load, the components of the mixture to be separated can interfere, and the elution peaks can be modified. A favorable case occurs when the most retained component has the highest saturation capacity. In that case, the most retained component pushes the least retained component ahead of it, and the separation can actually be much better than could be expected from elution mechanisms. Because of this "displacement effect," high load separation can actually be superior to separation under elution conditions. When good displacement conditions are obtained, a batch column can be overloaded beyond the level expected from evaluation of data determined with analytical chromatograms of individual components. In batch displacement chromatography, the retained component with high saturation capacity, referred to as the "displacer," is most often a molecule chosen for its useful displacement characteristics, and is not necessarily a component of the mixture to be separated.

There remains a need for an improved SMB method for purifying sucrose solutions wherein the sucrose-containing product is not contaminated by cross-over nonsucroses, the betaine and/or invert are recovered almost completely, and the advantages of SMB chromatography are not compromised.

DISCLOSURE OF INVENTION

In general terms, this invention constitutes an improvement to a simulated moving bed process for the recovery of a first product fraction predominating in a first product species from a liquid mixture containing that first product species in admixture with a second byproduct species. A feed stock is introduced to a recycle stream circulating through a partitioned bed of resin, raffinate is withdrawn from the recycle stream downstream from the introduction of the feed stock, eluent is introduced to the recycle stream downstream from the withdrawal of raffinate, and extract is withdrawn from the recycle stream downstream from the introduction of eluent, all in usual SMB fashion. The feed stock usually comprises a relatively large amount of the product species and a relatively small amount of the byproduct species.

The improvement of this invention generally comprises establishing a continuous simulated moving bed system in which a feed stock, comprising a relatively large amount of a product species and a relatively small amount of a byproduct species, is fed into a recycle stream circulating through a partitioned bed of resin, the recycle stream being characterized by a separation profile. A raffinate, comprising separated product species and containing other contaminant species, is removed from the recycle stream in the vicinity of the leading edge of the separation profile, downstream from the introduction of feed stock. Eluent is introduced to the recycle stream downstream from the withdrawal of raffinate, and an extract, comprising separated byproduct species, is withdrawn from the recycle stream downstream from the introduction of eluent, in the vicinity of the trailing edge of the separation profile. A significant improvement constitutes accumulating into the recycle stream sufficient displacer species to displace portions of the product species toward the leading edge of the separation profile of the recycle stream. Ideally, the displacer species is the byproduct species.

From another view, in the operation of a continuous simulated moving bed system to separate the components of a feed stock, wherein a resin bed is divided into a series of discrete vessels, each of which functions as a zone within a circulation loop through which is maintained a relatively large-volume continuous recycle stream, and a manifold system connects the vessels and directs in appropriate sequence to each such vessel relatively small-volume streams of feed stock and eluent, respectively, and from each vessel relatively small-volume streams of extract and raffinate, respectively, whereby to develop a circulating inventory of chromatographically separated chemical species characterized by a separation profile including an intermediate region occupied by a commercially valuable phase bounded by a trailing region and a leading region, the invention offers an improvement which comprises operating the system to establish a high inventory of a trailing separated species, whereby to displace a commercially valuable separated species into that leading region, and collecting a raffinate stream from that leading region of the separation profile of the recycle stream.

According to certain practical embodiments of this invention, betaine and/or invert is removed from sucrose solutions via SMB chromatography in near totality prior to purification of the sucrose. These two separations are ideally conducted in coupled SMB systems, with the raffinate produced by the first SMB (SMB A) being processed by a second SMB (SMB B). Independent and different operating parameters (appropriate for each SMB), independent inventory profiles, and independent continuous internal recycle loops are employed for these two respective operations.

The advantageous functions of SMB chromatography are insured by maintaining inventory build-up and continuous internal circulation on each SMB. The betaine and/or invert are recovered in near totality from a first extract fraction. The sucrose product, recovered as an extract from the raffinate fraction resulting from recovery of the first extract fraction, is of substantially higher purity than that produced by conventional operation due to the near total elimination of the crossover nonsucroses (betaine/invert).

In general, this invention may be viewed as an improvement over a simulated moving bed process for the recovery of sucrose from a raw sugar solution in which a feed stock is introduced to a recycle stream circulating through a partitioned bed of resin, raffinate is withdrawn (as a small-volume "sample") from that recycle stream downstream from the introduction of the feed stock, a compensating volume of water is introduced to that recycle stream downstream from the withdrawal of the raffinate, and a balancing "sample" amount of sucrose is withdrawn from that recycle stream downstream from the introduction of water. The purity of the sucrose recovered from SMB processing is enhanced in accordance with this invention by establishing first and second chromatographic procedures, the first of which is a continuous SMB, and the second of which can be of any convenient chromatographic configuration, including continuous SMB, sequential SMB or batch configurations. Continuous simulated moving bed configurations are currently preferred for both the first and second chromatographic procedures, and this disclosure makes primary reference to configurations which couple two continuous simulated moving beds, designated for convenience, SMB A and SMB B.

SMB A is operated such that a first feed stock, comprising sucrose and nonsucroses, is fed into a first recycle stream circulating through a first partitioned bed of resin; a first raffinate, comprising sucrose, ash and high molecular weight compounds separated from the feed stock, is removed from the first recycle stream downstream from the introduction of the first feed stock; water is introduced to the first recycle stream downstream from the withdrawal of the first raffinate; and a first extract, comprising nonsucroses separated from the first feed stock, is withdrawn from the first recycle stream downstream from the introduction of water. A second simulated moving bed, SMB B, is operated such that a second feed stock, comprising the first raffinate (from SMB A), is fed into a second recycle stream circulating through a second partitioned bed of resin; a second raffinate, comprising ash and high molecular weight compounds separated from the first raffinate, is removed from the second recycle stream downstream from the introduction of the second feed stock; water is introduced to the second recycle stream downstream from the withdrawal of the second raffinate; and a second extract, comprising sucrose, is withdrawn from the second recycle stream downstream from the introduction of water.

Broadly, the invention can be viewed as a type of "displacement chromatography" applied to a simulated moving bed operation. This mechanism results in remarkable and unexpected improved efficiency of separation. According to this invention, forcing a very high steady state inventory of small trailing organic molecules in a simulated moving bed causes a useful "displacement effect." Unlike batch displacement chromatography, the displacer is maintained in an equilibrated state, thereby providing a type of "continuous displacement chromatography." With sucrose mixtures, such as sugar beet or sugar cane solutions, the displacer is ideally part of the feed mixture, rather than an added component. The practice of the novel continuous displacement chromatography of this invention offers several unique and advantageous characteristics when applied to sucrose solutions. For example:

1. Because displacement rather than elution is key to the separation mechanism, the quantity of eluent used to separate the small organic molecules from the sucrose is very low. Water added to a chromatographic separation process must generally be recovered. Thus, a low requirement for water addition is economically advantageous. Typical molasses chromatographic separation systems use ratios of about 6.0–8.0 water volume for each volume of feed molasses (assuming the feed is 60% dissolved solids). By contrast, the displacement procedure of this invention permits the small trailing organic compounds to be separated almost entirely from the sucrose with water-to-feed ratios of 2.0 or less.

2. The displacement effect results in greater than 90% separation of the trailing small organic molecules, such as betaine, from the sucrose. These compounds are usually difficult to separate from the sucrose in industrial scale operations.

3. The concentration of the small organic molecule fraction is very high compared with the corresponding fraction recovered through elution techniques. Assuming an initial molasses of 60 purity and 60% dissolved solids, elution techniques typically yield betaine-containing fractions of 1% to 5% dissolved solids. With the disclosed displacement method, typical betaine-containing fractions contain about 8% to 15% dissolved solids.

4. The displacement effect forces a very high recovery of the sucrose, typically greater than 99%. It has not previously been recognized that building a large inventory of nonsucrose in a chromatographic separator will improve the sucrose recovery.

5. In conventional industrial sucrose elution chromatography, with strong cation ion exchange resins as the stationary phase, sucrose is a preferentially adsorbed component. As a result, the sucrose is collected somewhere roughly from the middle to the trailing edge of the developed elution profile. In contrast, the displacement procedure of this invention results in sucrose being pushed in exactly the opposite direction—into the area of the leading edge. The key advantage of this contradictory effect is that the sucrose is collected with conventionally easily separated leading edge components such as ash and very high molecular weight compounds. The coupled simulated moving bed aspect of this invention is, therefore, greatly enhanced because the difficult-to-remove small organic nonsucroses are absent following a first SMB so that a subsequent second SMB operating in a conventional manner can recover the sucrose at extremely high purity. Purities of final sucrose fractions from sugar beet molasses have been observed to exceed 97% on dissolved solids. High purity products are generally advantageous, and in this case, the benefits include improved processing characteristics, such as faster crystallization kinetics and lower product odor.

6. The final sucrose fraction is typically subjected to crystallization to obtain the sucrose as a pure product along with a second molasses. The new process of this invention is capable of producing a 96% purity sucrose fraction at 96% recovery so that the overall recovery of product sucrose after the combined operations of chromatographic separation and crystallization increases from the present practical standard of 78% to a new practical standard of about 90%.

7. Simulated moving bed operations require a certain length of time (number of cycles) to equilibrate. With the procedure of this invention, equilibration time can be reduced by adding previously stored or prepared small organic molecule fraction to the feed material or to an appropriate location in the chromatographic separator.

BRIEF DESCRIPTION OF THE DRAWINGS

In the drawings, which illustrate what is currently regarded as the best mode for carrying out the invention.

BEST MODES FOR CARRYING OUT THE INVENTION

Figure 1:
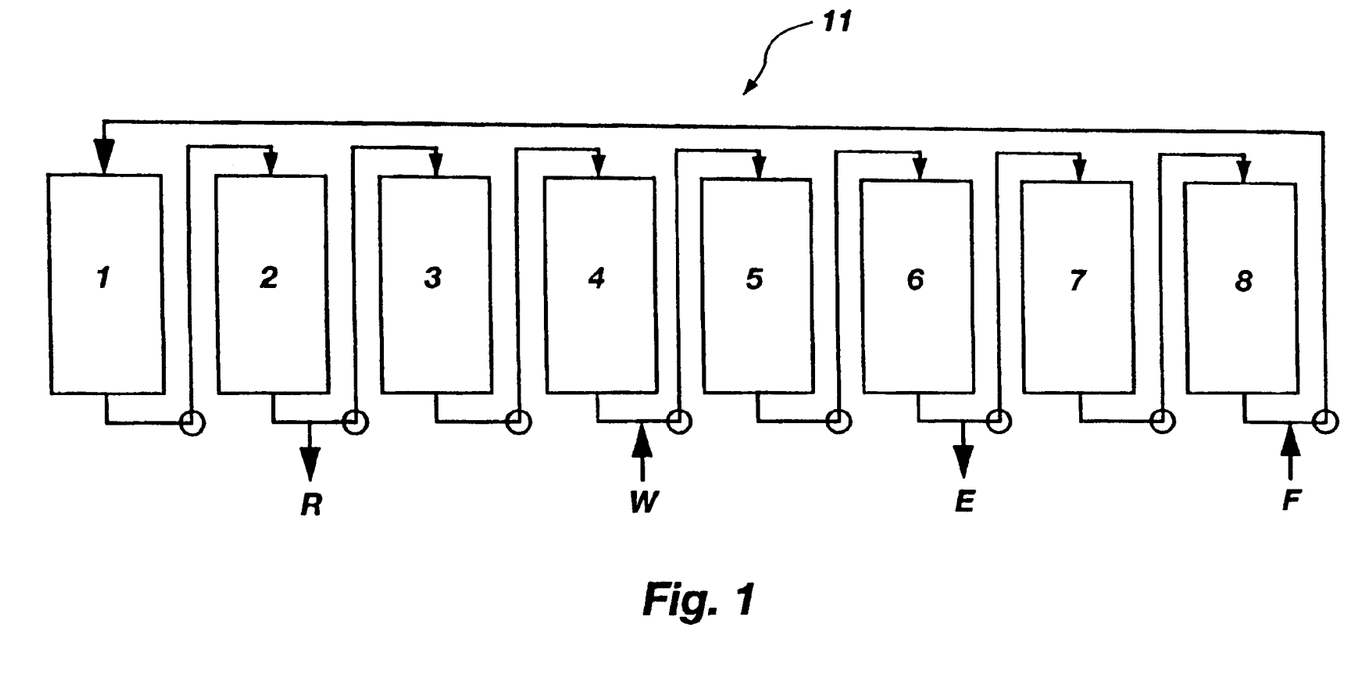
FIG. 1 is a simplified flow diagram of an SMB system typical of a conventional ion exclusion process.

As best illustrated by FIG. 1, eight cells (each comprising one or more vessels) are arranged to receive flow in series, all as explained in detail in U.S. Pat. No. 4,412,866. The cells are designated 1 through 8, respectively. A recycle, or circulation, stream flows continuously at a "basic" flow rate through the loop including the cells, 1–8, and a connecting manifold system, designated generally 11. The manifold 11 is configured to introduce feed stock F to the circulation stream exiting cell 8 as it flows to the top of cell 1 to withdraw raffinate R from the circulation stream exiting the bottom of cell 2, to introduce water W to the circulation stream entering the top of cell 5 and to withdraw extract E from the circulation stream exiting cell 6. These streams divide the total resin bed in the system into four zones, each of which comprises at least one cell. The extract stream contains the purified sucrose with typical betaine and/or invert contamination. The raffinate stream contains the remaining betaine and invert, ash and high molecular weight compounds. Typically, the resin used for the chromatographic separation is a monovalent form strong cation ion exchange resin.

In a typical SMB system, the manifold system 11 operates to shift each input, F and W, and each of the outputs, R and E, as a group to other locations around the loop. The specific SMB system illustrated is controlled through 8 steps. Accordingly, feed stock F will, in turn, be introduced in sequence to the tops of each of columns 1 through 8, while each of the other input and output streams will be similarly advanced to maintain their respective positions in the loop.

Figure 2:
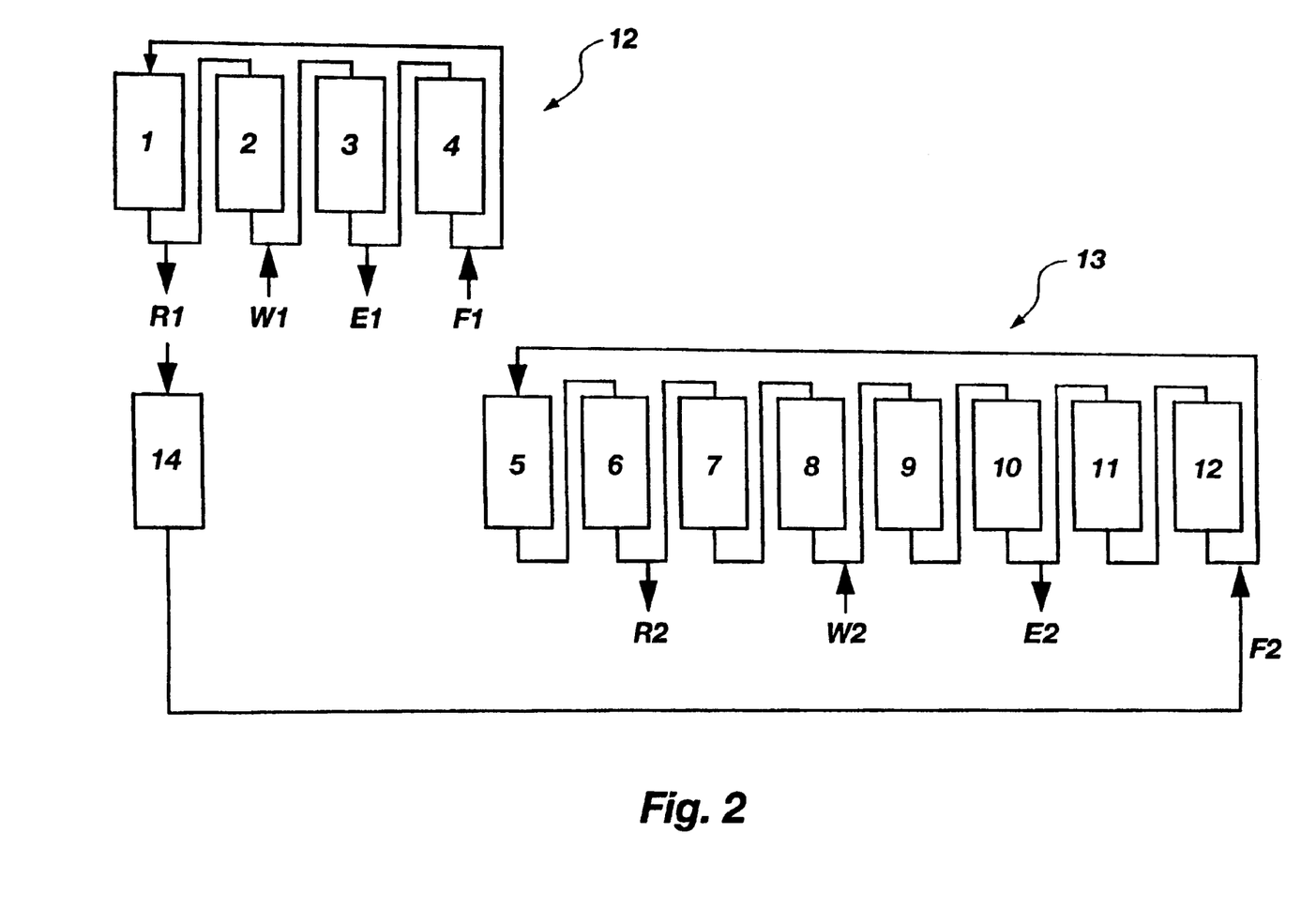
FIG. 2 is a simplified flow diagram of a coupled SMB system which allows for realization of this invention.

The arrangement illustrated by FIG. 2 allows for the recovery of betaine and/or invert prior to sucrose purification. In SMB A, designated generally 12, feed stock F1 is introduced to the circulation loop exiting cell 4 while water W1 is simultaneously introduced to the circulation loop exiting cell 2, extract E1 is removed from the circulation loop exiting cell 3 and raffinate R1 is removed from the circulation loop exiting cell 1. F1 is a sucrose solution containing betaine and/or invert components. E1 is an extract stream and contains the separated betaine and/or invert components. R1 is a raffinate stream and contains the separated sucrose, ash and high molecular weight compounds. It is noted that in the usual operation of a simulated moving bed, e.g., as described with reference to FIG. 1, the sucrose exits with the extract. In this respect, SMB A of this invention operates in a reverse manner as compared to conventional methods.

In SMB B, designated generally 13, operation is generally as described with reference to FIG. 1, except that feed stock F2 consists of raffinate from SMB A, extract E2 is sucrose product separated from ash and high molecular weight compounds, and raffinate R2 is the separated ash and high molecular weight compounds.

Although any number of separator cells appropriate for simulated moving bed operation may be used for either SMB A or SMB B (generally more cells yield improved separation), the betaine/invert separation provided by SMB A is sufficiently efficient that the four cells illustrated are generally adequate for this operation. Additional cells would ordinarily add to the cost of the process, without a corresponding benefit.

Concentrator 14, while not required, is a preferred component of the system. A high percent dry substance (% DS) feed is known to result in improved sucrose recovery. The concentrator 14 is thus desirably employed to raise the dry substance content of the raffinate from SMB A from a starting value of typically 25%–35% DS to a final value within the range of about 40% to about 70% DS before entering SMB B. The concentrator 14 can be of any conventional type, typically an evaporator system.

EXAMPLE 1

An equipment configuration as illustrated in FIG. 2 was evaluated. SMB A was operated using the disclosed displacement chromatography method. The 30 minute step time on SMB A was split into two periods of 15 minutes each. Recirculation was continuous during both periods, while feed, water, extract and raffinate were continuous during period 1. Such a configuration is useful to improve the efficiency of a four-cell SMB operation and is described in U.S. Pat. No. 5,102,553. Such a method is not generally beneficial when more cells are used for SMB A. SMB B was operated with all flows continuous (recirculation, feed, water, extract and raffinate).

The following operating parameters were used:

|  | SMB A | SMB B |
|---|---|---|
| Feed material | beet molasses | raffinate from SMB A |
| Feed (% DS) | 60 | 60* |
| Number of cells | 4 | 8 |
| Separation resin | Dow 350 micron monovalent strong cation resin | Dow 350 micron monovalent strong cation resin |
| Nonsucrose loading lbs/ft³ resin/day | 20 | 10 |
| Step time (time between switching valves to new position along the loop), minutes | 30 | 10 |
| Water/feed volume ratio | 2.0 | 5.6 |
| Extract/raffinate volume ratio | 0.5 | 0.2 |
| Continuous basic internal circulation rate, BV/hr | 0.29 | 0.35 |

*The raffinate from SMB A was increased in concentration to 60% DS (dissolved solids) prior to being fed to SMB B.

The following results were obtained:

|  | SMB A | SMB B |
|---|---|---|
| Feed % sucrose on D.S. (dry substance) | 60.4 | 69.0 |
| Feed % betaine on D.S, | 6.1 | 0.3 |
| Extract % sucrose on D.S. | 2.2 | 97.1 |
| Extract % betaine on D.S. | 50.0 | 0 |

Of particular note is the almost complete elimination of betaine across SMB A. Betaine is representative of the normally difficult-to-remove trailing small organic compounds in the system. As a result of their elimination, SMB B easily produces a very high final sucrose fraction (extract).

As presently understood, displacement chromatography induced on SMB A improves the recovery of the sucrose and the small organic molecules in their respective fractions. For sugar beet and sugar cane syrup applications, the displacement chromatography mechanism will take effect over several cycles, operated within parameters such as those indicated in EXAMPLE 1.

EXAMPLE 2

Figure 3:
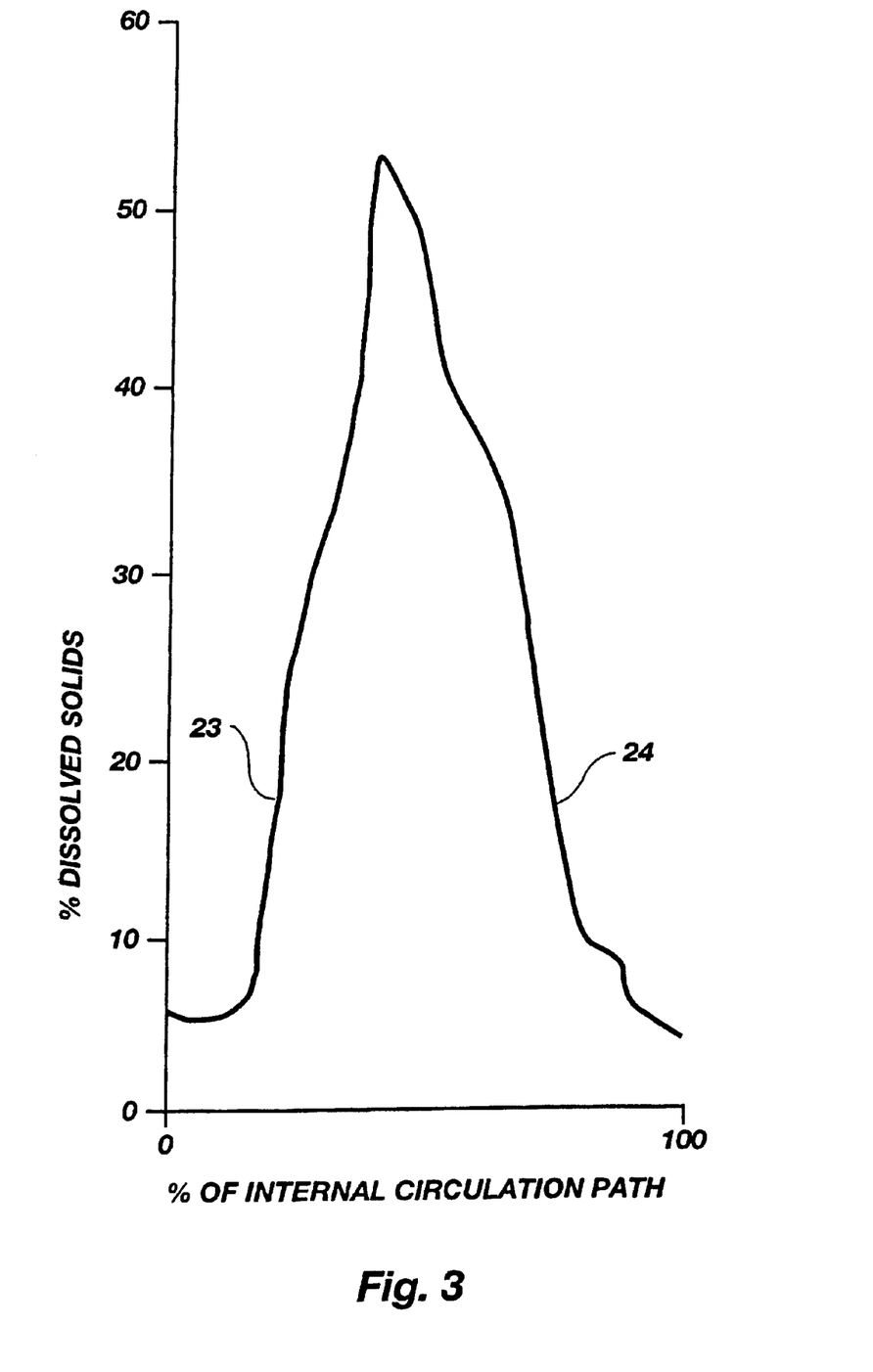
FIGS. 3 and 4 are drawings of chromatographic solids profiles pertinent to an embodiment of this invention.
Figure 4:
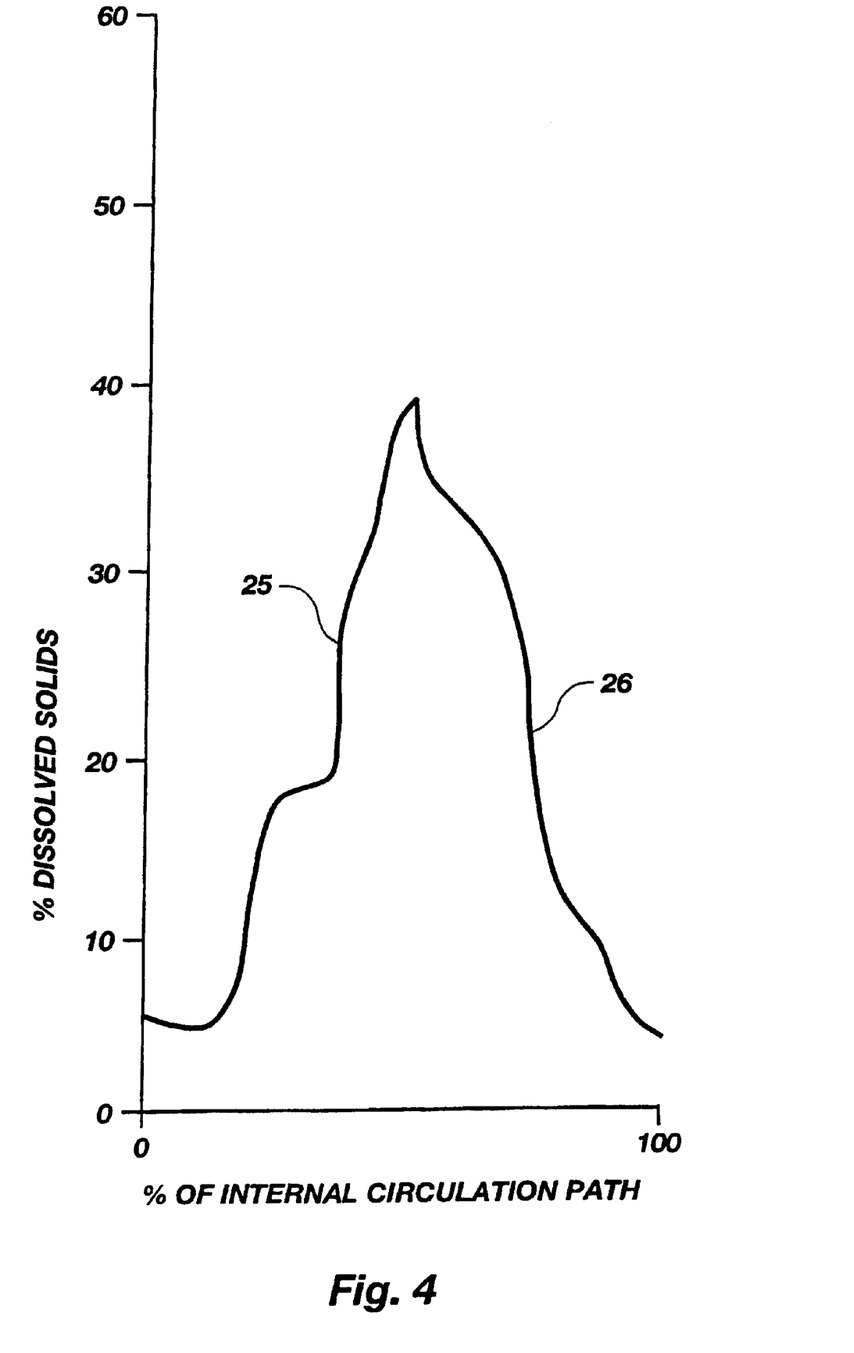

FIG. 3 illustrates the initial approach to equilibrium observed in SMB A prior to transition to displacement chromatography in a test run. Beet molasses is the feed material. In FIG. 3, "% dissolved solids concentration" is indicated on the vertical axis while "% of internal path length through the SMB" is indicated on the horizontal axis. This profile is in continuous circulation around the separator path. Under these conditions, the trailing area, 23, contains small organic compounds such as betaine and invert sugars; it also contains sucrose, which is in its conventional location for elution chromatography. The leading edge, 24, contains ash, poorly separated sucrose and high molecular weight compounds. As operation continues, the trailing small organic compounds begin to inventory. Although the specific time to transition is variable, after approximately 20–25 complete cycles, the % dissolved solids profile illustrated by FIG. 3 is observed to make a rather abrupt transition to the % dissolved solids profile illustrated by FIG. 4. This transition typically occurs over about 8 cycles. A trailing plateau, 25, forms from the inventory of small organic compounds and acts as a chromatographic displacer. At the end of the transition, the cumulative small molecule % on dissolved solids internal to the SMB is at a very high level compared to the concentration measured in the feed material. This differential inventory of the trailing small organic compounds causes the displacement mechanism to take effect. The sucrose is forced by the displacement mechanism to move into the leading edge area, 26. As a result, the sucrose is recovered at a level of 99% or greater in the leading edge raffinate and the trailing small organic molecules are recovered at a level of 90% or greater in the extract. The system remains in this equilibrated, continuous operating mode as long as feed material is provided—typically for several weeks or months.

In addition to the sudden change in the characteristics of the separation profile, the practice of this invention results in a decrease in the overall resin bed pressure drop by a factor of about 0.5. This decrease is due to the developed displacement front's pushing the sucrose conventionally found in the trailing area into the leading area, from which a large amount is expelled from the system. No change in operating parameters is required to cause the expulsion of the sucrose. It is an unattended effect which takes place as the transition to displacement occurs. Monitoring the total system pressure drop is, therefore, a useful way of determining the period of transition from elution to displacement chromatography. Prior to this invention, SMB systems have been observed to undergo an ever-increasing pressure drop as the systems fill with solids during equilibration. They do not undergo a sudden pressure drop collapse as is observed in the practice of this invention.

The displacement front characteristic of this invention may be formed more quickly by temporarily adding previously stored or recycled small organic molecule fraction (extract from SMB A) to the feed mixture. This expedient will allow the small molecule components to more quickly inventory inside the system. It is also possible to more quickly form the displacement front by first loading previously stored small organic molecule fraction (extract from SMB A) into the appropriate location of SMB A. A typical procedure is to adjust the stored or prepared small molecule fraction to about 15% DS and fill the column to be extracted with this material. With reference to FIG. 2, column 3 can initially be filled with the small molecule material prior to starting the system's operation. In addition to decreasing the time required for equilibration, such procedures can be helpful when separating high purity sucrose mixtures which may require a lengthy inventory period due to the low ratio of displacer molecules to sucrose.

Both the feed addition and the column loading approaches taught by this disclosure are applicable to the chromatographic separation of sugar beet or sugar cane raw juice as described in U.S. Pat. No. 5,466,294.

Another characteristic of the displacement process of this invention is that the raffinate product from SMB A can be of relatively low sucrose purity. The reason for this beneficial consequence is that the nonsucrose in this raffinate is comprised of materials which are easily separated in SMB B. With the displacement process, typical raffinate purities from SMB A can be as low as 65% to 75% sucrose on dissolved solids. This range of raffinate purities from SMB A is sufficient to easily obtain sucrose fraction purities greater than 95% from SMB B.

Unlike conventional elution chromatography, the displacement chromatography mode of this invention is caused by overloaded conditions. Accordingly, a much lower use of eluent is required. In ordinary elution chromatography, a decreased use of eluent is actually detrimental to separation efficiency. It is recommended that the ratio of water volume to sucrose mixture volume be in the approximate range of 1.0 to 3.0 for 60% dissolved solids molasses. This range can easily be calculated for molasses with other initial % dissolved solids. To calculate other cases, the total water in the water stream and the total water in the molasses stream are summed and adjusted to a constant. For example, the water-to-feed volume ratio will change as the molasses % dissolved solids changes in a specific instance as follows:

| Feed % dissolved solids | Water to Feed volume ratio |
| --- | --- |
| 60 | 2.0 |
| 50 | 1.4 |
| 40 | 0.83 |

Another variable which influences development of the displacement front of small molecules is the volume ratio of extract to raffinate. Removing only small fractions of extract helps cause the inventory effect to occur. Extract-to-raffinate volume ratios of about 0.2 to 0.6 are sufficient. Larger volume ratios can cause the small organic molecule inventory in the chromatographic separator to decrease and, therefore, return the separation mechanism to the less efficient elution mode.

The efficiency of operation of SMB A is influenced by the measure of nonsucroses loaded per unit of separation resin. Levels of 20 lbs. to 40 lbs. of nonsucrose fed per cubic foot of separation resin/day have been found to be appropriate to provide an efficient loading condition for the displacement mechanism. Less loading, while operable, generally constitutes an inefficient use of resin.

EXAMPLE 3

The cumulative contents of SMB A were collected to determine the extent of differential inventory of low molecular weight organic compounds which cause the displacement effect. For this test, sugar beet molasses was fed to SMB A until the separation profile in FIG. 3 collapsed to the equilibrated profile in FIG. 4. The operation was stopped, and all solids contained in the system were rinsed to a single container. Betaine was used as a molecule representative of the displacement components (trailing small organic molecules). Analysis demonstrated that the cumulative betaine in the equilibrated SMB A was 26.1% on dissolved solids. However, the feed material consisted of only 7.3% betaine on solids. Therefore, this result was understood to demonstrate that a large differential inventory of small organic molecules was effectively forced upon the internal equilibrated solids profile within SMB A. The displacement effect of this invention is attributable to this large inventory.

What is claimed is:

1. A method for processing a product containing solution in a chromatographic simulated moving bed, said method comprising:

feeding a feed solution containing a product and at least one small organic molecule to a simulated moving bed comprising at least one chromatographic resin bed;

establishing at least a separation profile within said simulated moving bed structure;

operating said simulated moving bed to allow accumulation of an inventory of said at least one small organic molecule in equilibrium, wherein said inventory displaces said product in said separation profile; and, producing a first stream comprising said product wherein said first stream comprises a higher concentration of said product on a dry solids basis than said feed solution and a lower concentration of said at least one small organic molecule on a dry solids basis than said feed solution.

2. The method according to claim 1 further including recovering said product from said first stream.

3. The method according to claim 2 further including purifying said first stream prior to recovering said product from said first steam.

4. The method according to claim 1 further including adding an additional solution comprising said at least one small organic molecule to said feed solution.

5. The method according to claim 4 further including producing a second stream containing said at least one small organic molecule and recovering at least one of said at least one small organic molecule from said second stream.

6. The method according to claim 1 further including feeding at least a part of the at least one chromatographic resin bed with at least one of said at least one small organic molecule prior to operating said simulated moving bed.

7. A method for processing sucrose-containing solutions in a chromatographic simulated moving bed, said method comprising:

feeding a sucrose-containing solution containing small organic molecules to a first chromatographic procedure involving at least one chromatographic resin bed;

subjecting said sucrose-containing solution to a recycle stream flowing through said at least one resin bed;

producing at least a first stream containing sucrose;

producing a second solution from said first stream; and, purifying said second solution through a second chromatographic procedure to produce a second stream comprising sucrose, wherein said second stream is free from a significant quantity of said at least one small organic molecule selected from the group consisting of betaine, invert, low molecular weight nonsucroses, crossover nonsugars and amino acids.

8. The method according to claim 7, wherein said at least one small organic molecule is betaine and said significant quantity of said betaine in said second stream contains sucrose containing less than one-tenth of one percent (0.1%) of said betaine on a dry solids basis.

9. The method according to claim 7, wherein said first chromatographic procedure is selected from the group consisting of an SMB procedure, simulated moving bed procedure, a continuous simulated moving bed procedure and a sequential simulated moving bed procedure.

10. A method for processing a product containing solution in a chromatographic simulated moving bed, said method comprising:

feeding a feed solution containing a product and at least one small organic molecule to a chromatographic bed comprises a series of discrete vessels in a loop;

establishing a flow in said chromatographic bed wherein said flow comprises said product and said at least one small organic molecule;

operating a recycle wherein said at least one small organic molecule displaces said product into a first phase of said flow, and displaces said at least one small organic molecule into a second phase of said flow; and producing a steam comprising said product wherein said stream contains a higher concentration of said product on a dry solids basis than said feed solution and a lower concentration of said at least one small organic molecule on a dry solids basis than said feed solution.

* * * * *